United States Patent [19]

Machida

[11] Patent Number: 5,709,211

[45] Date of Patent: Jan. 20, 1998

[54] ULTRASONIC DIAGNOSTIC APPARATUS

[75] Inventor: Etsuro Machida, Kawasaki, Japan

[73] Assignee: Fujitsu Limited, Kawasaki, Japan

[21] Appl. No.: 626,611

[22] Filed: Apr. 2, 1996

[30] Foreign Application Priority Data

Jun. 30, 1995 [JP] Japan .................................. 7-166250

[51] Int. Cl.$^6$ .................................................. A61B 8/06
[52] U.S. Cl. .................. 128/661.08; 128/660.05
[58] Field of Search .................. 128/661.09, 661.08, 128/660.05; 364/413.25

[56] References Cited

U.S. PATENT DOCUMENTS 4,217,909 8/1980 Papadofrangakis et al. ...... 128/660.05

*Primary Examiner*—Francis Jaworski
*Assistant Examiner*—Derrick Fields
*Attorney, Agent, or Firm*—Staas & Halsey

[57] ABSTRACT

An ultrasonic diagnostic apparatus having both functions of a color flow imaging function of displaying with color a blood flow distribution within the subject on a tomographic image of the subject and a pulse Doppler function of evaluating and displaying with great accuracy a blood flow velocity of a point to be observed which is designated within a tomographic plane. The ultrasonic diagnostic apparatus implements the pulse Doppler function through few operations as compared with the conventional one. A direction of the blood flow is evaluated on the basis of a blood flow distribution of the peripheral pixels of the point of interest to be observed, determined through the color flow imaging function.

12 Claims, 14 Drawing Sheets

Fig. 4

| MAX. COLOR DATA REGISTER |
|---|
| MAX. RETRIEVAL DIRECTION REGISTER |
| RETRIEVAL COUNTER |
| COLOR DATA COUNTER |

Fig. 6

| MAX. FLOW VELOCITY REGISTER |
| MAX. RETRIEVAL DIRECTION REGISTER |
| RETRIEVAL PIXEL COUNTER |
| COLOR DATA COUNTER |

| MAX. POSITION REGISTER |
| MAX. RETRIEVAL DIRECTION REG. |
| RETRIEVAL PIXEL COUNTER |
| SINGLE DIRECTION MAX. LENGTH REG. |
| PREVIOUS FLOW VELOCITY REG. |

Fig. 11

| |
|---|
| DIRECTION COLOR DATA COUNTER 1 |
| DIRECTION COLOR DATA COUNTER 2 |
| ⋮ |
| DIRECTION COLOR DATA COUNTER n |
| DIRECTION MAX. FLOW VELOCITY REG. 1 |
| DIRECTION MAX. FLOW VELOCITY REG. 2 |
| ⋮ |
| DIRECTION MAX. FLOW VELOCITY REG. n |
| DIRECTION MAX. LENGTH REG. 1 |
| DIRECTION MAX. LENGTH REG. 2 |
| ⋮ |
| DIRECTION MAX. LENGTH REG. n |
| RETRIEVAL PIXEL COUNTER |
| TEMPORARY FLAG |
| DIRECTION EVALUATION VALUE REG. 1 |
| DIRECTION EVALUATION VALUE REG. 2 |
| ⋮ |
| DIRECTION EVALUATION VALUE REG. n |

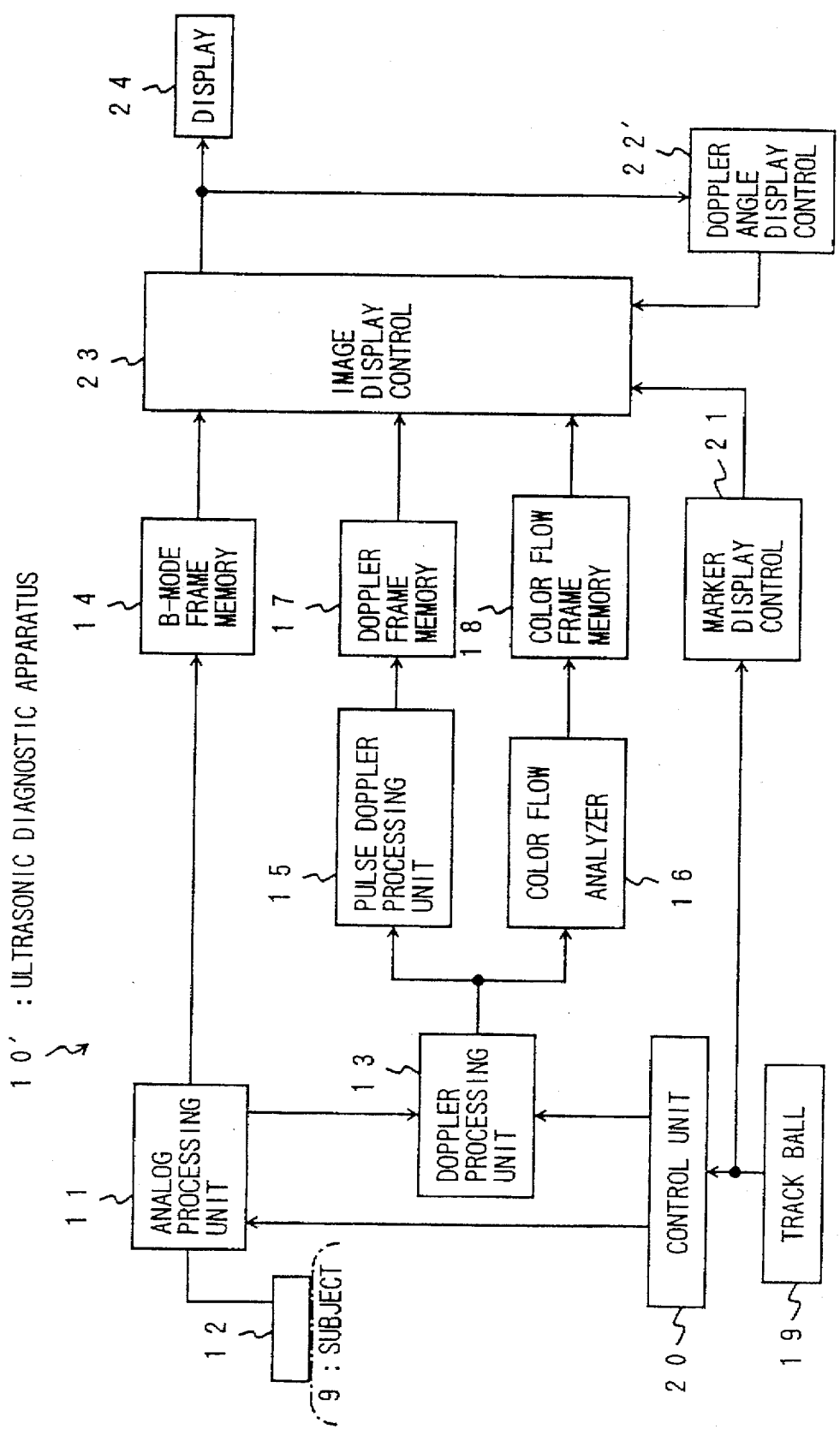

| MAX. DISTANCE REGISTER |
| --- |
| HOR LINE COUNTER |
| RETRIEVAL PIXEL COUNTER |
| TEMP. FLAG |
| PREVIOUS FLOW VELOCITY REG |
| MAX. POSITION REG (x) |
| MAX. POSITION REG (y) |

5,709,211

ULTRASONIC DIAGNOSTIC APPARATUS

BACKGROUND OF THE INVENTION

1. Field of the Invention

The present invention relates to an ultrasonic diagnostic apparatus in which ultrasonic wave beams are transmitted and ultrasonic waves reflected within the subject are received to form received signals, and information within the subject is displayed on the basis of the received signals, and more particularly to an ultrasonic diagnostic apparatus having both functions of a so-called color flow imaging function of displaying with color a blood flow distribution within the subject on a tomographic image of the subject and a so-called pulse Doppler function of evaluating and displaying with great accuracy a blood flow velocity of a point to be observed which is designated within a tomographic plane.

2. Description of the Related Art

Hitherto, there has been used an ultrasonic diagnostic apparatus in which ultrasonic waves are transmitted toward the subject, specially a living body, ultrasonic waves reflecting from a tissue within the living body are received to generate received signals, and a tomographic image of the living body is displayed on the basis of the received signals, thereby facilitating a diagnostic of diseases of the viscus inner organ or the like in the living body.

Among such ultrasonic diagnostic apparatuses, there is one which is so arranged that ultrasonic waves reflected on a blood flow in the body are received to derive a blood flow velocity so that the resultant blood flow velocity can be displayed. With respect to schemes in which the resultant blood flow velocity is displayed, there are two kinds of schemes. According to one of the schemes, a blood flow distribution within a tomographic plane or a partial area of the tomographic plane is superposed on a white and black tomographic image; for example, a blood flow of which a direction approaches the body surface is displayed by red and a blood flow of which a direction goes away from the body surface is displayed by blue; and a blood flow velocity of the respective pixel is displayed by depth of red and blue. This scheme is referred to as a color flow imaging. A blood flow velocity data, which is formed in accordance with the above-mentioned scheme, is referred to as "color data" hereinafter. This scheme is effective in an intuitive grasp of the blood flow distribution. In this scheme, since there is a need to evaluate at high speed an extensive blood flow velocity distribution, a blood flow velocity is evaluated through, for example, performing an arithmetic operation for auto-correlation suitable for a high speed arithmetic operation. However, according to such an arithmetic operation, at the request of the high speed processing, data per pixel to be used in the arithmetic operation are few in number. As a result, there is included a considerably large erroneous primary factor. Therefore, it is difficult to evaluate a blood flow velocity with great accuracy.

Another of the schemes in which the resultant blood flow velocity is displayed is a scheme in which a blood flow velocity on some point within the subject is evaluated and then displayed. It is sufficient for this scheme to evaluate a blood flow velocity of only some point (a point to be observed). Therefore, it is possible to collect a large number of data on the point in a short time, and thus it is possible to evaluate a blood flow velocity with great accuracy on the basis of the large number of data thus collected, by the use of, for example, an FFT (Fast Fourier Transform). As this scheme, there is well known a scheme in which a blood flow velocity is evaluated utilizing a Doppler phenomenon to ultrasonic pulses. Here, such a scheme is referred to as a pulse Doppler scheme. A blood flow velocity data, which is formed in accordance with the above-mentioned pulse Doppler scheme, is referred to as "Doppler data" hereinafter.

According to the pulse Doppler scheme, it is possible to evaluate a blood flow velocity with great accuracy. However, since a blood flow velocity on one point is simply known, there is adopted a procedure in which a point of interest to be observed is found through, for example, the color flow imaging, the point of interest is designated, and a blood flow velocity is measured with great accuracy.

By the way, in case of the pulse Doppler scheme, the blood flow velocity to be directly measured is a blood flow velocity component as to a direction in which an ultrasonic pulse beam extends. Hence, for instance, in a case where a blood flow direction on the point of interest has an angle θ other than 0° with respect to the ultrasonic pulse beam direction, V cosθ is measured, where V denotes an actual blood flow velocity. This angle is referred to as "Doppler angle". Accordingly, in order to determine the accurate blood flow velocity, it is necessary to know a Doppler angle at the point of interest and convert the measured blood flow velocity in accordance with the Doppler angle.

Incidentally, also in case of the color flow imaging, there is measured a blood flow velocity component as to a direction in which an ultrasonic pulse beam extends. In case of the color flow imaging, however, it aims to grasp the blood flow distribution in its entirety and thus there is no problem on errors in a blood flow velocity.

To perform a conversion of the blood flow velocity involved in the blood flow direction in the pulse Doppler scheme, the conventional ultrasonic diagnostic apparatus is arranged in such a way that a mark (for example, an arrow) indicating a blood flow direction extending from a point of interest is displayed on a display screen in accordance with a color flow imaging scheme, and an operator manipulates a predetermined handler, while looking at the display screen, to adjust the mark to a direction of the blood flow, thereby informing the apparatus of the Doppler angle. The apparatus converts the blood flow velocity on the point of interest on the basis of the Doppler angle entered by the operator's operation.

FIG. 16 is a view illustrating an example of a display screen of an ultrasonic diagnostic apparatus.

On the left half of the display screen 1, there is displayed a sector configuration of tomographic image of the subject (a so-called B-mode image). A color flow image is superposed on the B-mode image 2 so that a blood vessel 3 is displayed with a color.

Here, a point P of interest to be observed is set up in the blood vessel 3 through manipulation of a handler not illustrated. At that time, an ultrasonic pulse beam passing through the point P of interest extends in a direction from a point Q through the point P to a point R. Next, a Doppler angle is set up. On the B-mode image 2, there is displayed a arrow 4 which ought to be adjusted to a blood flow direction. Manipulation of the handler not illustrated permits the arrow 4 to rotate on the point P of interest. Thus, the arrow 4 is set up through manipulation of the handler to meet the blood flow direction (or a direction in which the blood vessel extends) as illustrated. In this manner, the Doppler angle θ is set up.

On the other hand, on the right half of FIG. 16, there is displayed blood flow velocity on the point P of interest, which has been detected in accordance with the pulse Doppler scheme. The axis of abscissas denotes time, and the axis of ordinates denotes blood flow velocity on the respective time, on the point P of interest. In FIG. 16, there is appended a scale at the side of the curve representative of the blood flow velocity. The scale is altered in accordance with the Doppler angle θ entered through manipulation as mentioned above. While it is of course possible to vary the amplitude of the curve representative of the blood flow velocity in compliance with the Doppler angle θ, here the scale is varied without changing the amplitude of the curve, since too much reduction or enlargement of the amplitude of the curve will make it difficult to observe the curve.

If it is desired to know the exact blood flow velocity using the pulse Doppler scheme, it is recommended that the Doppler angle is exactly set in accordance with the manner as mentioned above. It is troublesome, however, for the busy clinical situation to set the Doppler angle every one, and this work will take a great deal of time. This respect is an obstacle to an effective practical use of the function of the pulse Doppler.

SUMMARY OF THE INVENTION

In view of the foregoing, it is therefore an object of the present invention to provide an ultrasonic diagnostic apparatus capable of detecting the accurate blood flow velocity on a point of interest to be observed through few operations as compared with the conventional one.

To achieve the above-mentioned objects, according to the present invention, there is provided an ultrasonic diagnostic apparatus in which ultrasonic beams are transmitted into a subject and ultrasonic waves reflected within the subject are received thereby forming received signals, and information as to the inside of the subject is displayed on the basis of the thus obtained received signals, the ultrasonic diagnostic apparatus comprising:

(1) first blood flow velocity measurement means for evaluating on the basis of the received signals a blood flow velocity distribution covering a plurality of pixels within a tomographic plane spreading on a two-dimensional basis within the subject;

(2) observed point setting means for optionally setting a point of interest to be observed within the tomographic plane;

(3) second blood flow velocity measurement means for evaluating on the basis of the received signals a blood flow velocity, at the point of interest set by said observed point setting means, in a direction in which ultrasonic beams passing through the point of interest are extended, said second blood flow velocity measurement means evaluating the blood flow velocity with greater accuracy than said first blood flow velocity measurement means;

(4) blood flow direction arithmetic means for evaluating a direction of a blood flow at the point of interest within said tomographic plane on the basis of the blood flow velocity distribution evaluated by said first blood flow velocity measurement means; and (5) blood flow velocity conversion means for converting the blood flow velocity at the point of interest evaluated by said second blood flow velocity measurement means into a blood flow velocity in the direction of the blood flow evaluated by said blood flow direction arithmetic means.

Here, it is acceptable that said blood flow direction arithmetic means evaluates, on the basis of the blood flow velocity distribution evaluated by said first blood flow velocity measurement means, evaluation values each involved in an associated one of a plurality of segments radially extending from the point of interest within the tomographic plane, representative of a probability such that the direction in which the respective segment extends is a direction of a blood flow at the point of interest, and determines, as the direction of the blood flow, a direction in which the segment involved in the maximum evaluation value of all the plurality of segments extends.

In this case, it is acceptable that said blood flow direction arithmetic means evaluates a number of pixels on which the blood flow exists, said pixels being located on each of the plurality of segments extending in a predetermined area including the point of interest within the tomographic plane, for each segment, and uses the number of pixels as the evaluation values; said blood flow direction arithmetic means evaluates a maximum flow velocity of all the blood flow velocity messages on pixels, said pixels being located on each of the plurality of segments extending in a predetermined area including the point of interest within the tomographic plane, for each segment, and uses the maximum flow velocity as the evaluation values; or said blood flow direction arithmetic means evaluates a distance starting from the point of interest up to the farthest pixel involved in a blood flow existence continued from the point of interest, of all the pixels on which the blood flow exist in a direction along each of the plurality of segments extending in a predetermined area including the point of interest within the tomographic plane, for each segment, and uses the distance thus obtained as the evaluation values.

Further, it is acceptable that said blood flow direction arithmetic means evaluates at least two among a number of pixels on which the blood flow exists, said pixels being located on each of the plurality of segments extending in a predetermined area including the point of interest within the tomographic plane, a maximum flow velocity of all the blood flow velocity messages on said pixels, and a distance starting from the point of interest up to the farthest pixel involved in a blood flow existence continued from the point of interest, of all the pixels on which the blood flow exist in a direction along each of the plurality of segments, for each segment, and determines the evaluation values for each segment on the basis of said at least two ones.

Still further, it is acceptable that said blood flow direction arithmetic means compares the maximum evaluation value with a predetermined threshold, and as a result when the the maximum evaluation value is less than the threshold, issues information indicating that conversion of the blood flow velocity by said blood flow velocity conversion means is not feasible; or said blood flow direction arithmetic means compares the maximum evaluation value with a predetermined threshold, and as a result when the the maximum evaluation value is less than threshold, determines that a predetermined direction within said tomographic plane is a direction of the blood flow at the point of interest.

In the ultrasonic diagnostic apparatus according to the present invention, as described above, it is acceptable that said blood flow direction arithmetic means determines, on the basis of the blood flow velocity distribution evaluated by said first blood flow velocity measurement means, at least one end point of each of segment areas involved in a continuity in pixels involving the existence of a blood flow, along each of a plurality of segments extending in mutually parallel directions within said tomographic plane, and determines a direction directed from the point of interest toward the end point involved in the longest distance between the point of interest and the end point, of all the end points, as a direction of the blood flow at the point of interest.

Incidentally, it is acceptable that said blood flow direction arithmetic means regards, even if the pixels involved in the absence of the blood flow in a direction along each of the segments continue below a predetermined number, these pixels continued below the predetermined number as the pixels involved in the presence of the blood flow.

To evaluate the blood flow velocity according to the pulse Doppler scheme, usually, a point of interest to be observed is set in accordance with the color flow image function. In other words, it is general that the ultrasonic diagnostic apparatus, which has a measurement function for the blood flow velocity according to the pulse Doppler scheme, is provided with the color flow image function.

The present invention has been made in view of the foregoing. According to the ultrasonic diagnostic apparatus as mentioned above, a blood flow direction (Doppler angle) is determined on the basis of the blood flow velocity distribution (color data) evaluated by said first blood flow velocity measurement means, and the blood flow velocity (Doppler data) at the point of interest evaluated by said second blood flow velocity measurement means is converted on the basis of the determined blood flow direction. According to the ultrasonic diagnostic apparatus of the present invention, it is possible for an observer or operator to evaluate a blood flow velocity at the point of interest with great accuracy taking account of the Doppler angle, simply through a designation of the point of interest to be observed within the tomographic plane, without an entry of information as to the Doppler angle through a manual operation. Thus, according to the present invention, there is simplified an operation for determined a proper blood flow velocity at the point of interest taking account of the Doppler angle. This feature contributes to the reduction of diagnostic time and a higher precision of diagnosis.

To evaluate the blood flow velocity on the point of interest, it is acceptable that on the basis of the blood flow velocity distribution evaluated by said first blood flow velocity measurement means, evaluated are evaluation values each involved in an associated one of a plurality of segments radially extending, for example, from the point of interest within the tomographic plane, representative of a probability such that the direction in which the respective segment extends is a direction of a blood flow at the point of interest, and a direction in which the segment involved in the maximum evaluation value of all the plurality of segments extends is determined as the direction of the blood flow.

As the evaluation values at that time, it is possible to adopted one or a combination of a number of pixels on which the blood flow exists, said pixels being located on each of the plurality of segments extending in a predetermined area including the point of interest within the tomographic plane, a maximum flow velocity of all the blood flow velocity messages on said pixels, and a distance starting from the point of interest up to the farthest pixel involved in a blood flow existence continued from the point of interest, of all the pixels on which the blood flow exist in a direction along each of the plurality of segments.

Here, in a case where a direction of the blood flow is not determined with accuracy in accordance with the above-mentioned scheme, in other words, when the maximum evaluation value is compared with a predetermined threshold and the maximum evaluation value is less than the threshold, it is acceptable that issued is information indicating that conversion of the blood flow velocity by said blood flow velocity conversion means is not feasible and if necessary such information is displayed; or together with the issuance of such information or alternatively, it is determined that a predetermined direction within said tomographic plane, for example, a direction in which the ultrasonic pulse beam extends, is a direction of the blood flow at the point of interest.

Further, in the ultrasonic diagnostic apparatus according to the present invention, as described above, to determine the blood flow velocity at the point of interest, there is adopted an arithmetic operation in which determined is, on the basis of the blood flow velocity distribution evaluated by said first blood flow velocity measurement means, at least one end point of each of segment areas involved in a continuity in pixels involving the existence of a blood flow, along each of a plurality of segments extending in mutually parallel directions within said tomographic plane, and determined is a direction directed from the point of interest toward the end point involved in the longest distance between the point of interest and the end point, of all the end points, as a direction of the blood flow at the point of interest. This feature makes it possible to implement a higher speed of operation for looking for a blood flow direction, and in addition to determine the blood flow direction with great accuracy sufficient for a practical use.

Incidentally, according to the blood flow velocity arithmetic operation in the color flow imaging, since it involves large errors, it happens that in spite of the existence of the blood flow indeed, no color data exists (this means that no blood flow exists or only minute blood flow exists). For this reason, it is preferable that said blood flow direction arithmetic means regards, even if the pixels involved in the absence of the blood flow in a direction along each of the segments continue below a predetermined number, these pixels continued below the predetermined number as the pixels involved in the presence of the blood flow, that is, the pixels involved in the presence of the color data.

BRIEF DESCRIPTION OF THE DRAWINGS

FIG. 4 is an illustration showing a list for registers and the like appearing in the flowchart of FIG. 3;

FIG. 6 is an illustration showing a list for registers and the like appearing in the flowchart of FIG. 5;

FIG. 11 is an illustration showing a list for registers and the like appearing in the flowchart of FIG. 10;

FIG. 12 is a block diagram of an ultrasonic diagnostic apparatus according to an another illustrative embodiment of the present invention;

DESCRIPTION OF THE PREFERRED EMBODIMENTS

Hereinafter, there will be described embodiments of the present invention.

Figure 1:
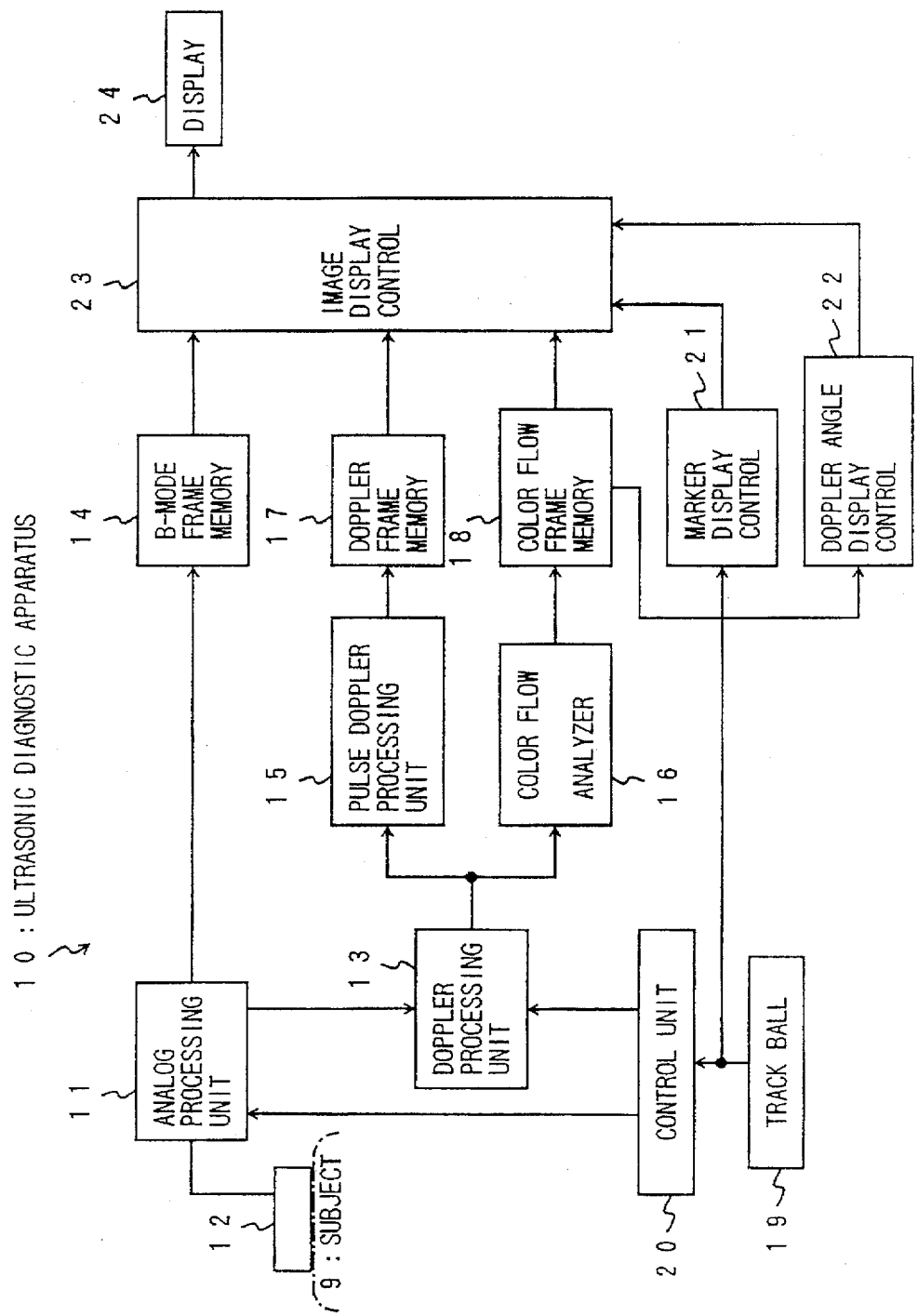
FIG. 1 is a block diagram of an ultrasonic diagnostic apparatus according to an illustrative embodiment of the present invention.

FIG. 1 is a block diagram of an ultrasonic diagnostic apparatus according to an illustrative embodiment of the present invention.

Figures 15, 16:
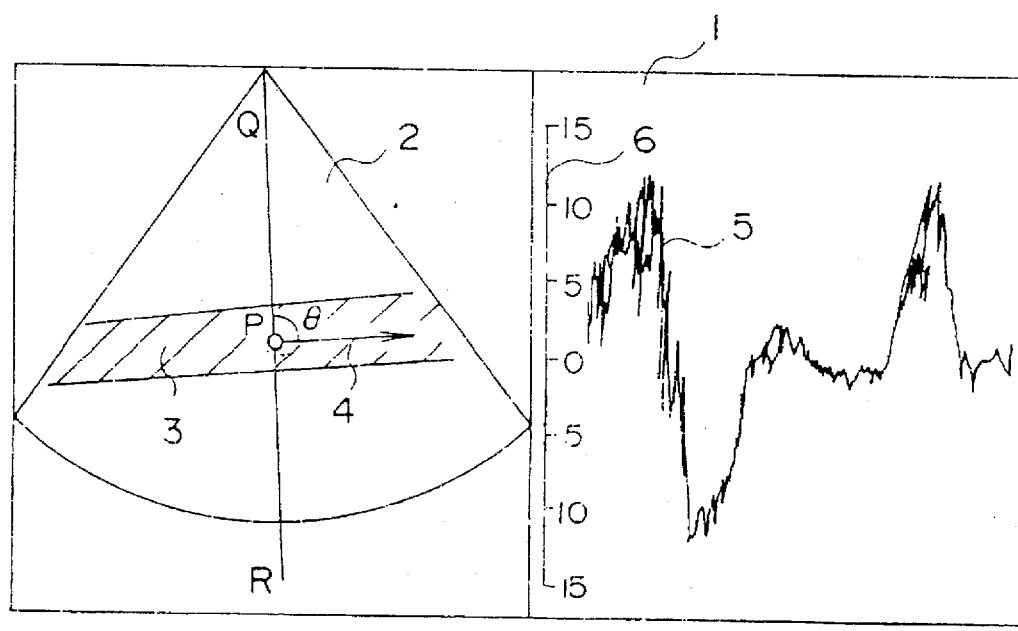
FIG. 15 is an illustration showing a list for registers and the like appearing in the flowchart of FIG. 14.
FIG. 16 is an illustration of a display screen of an ultrasonic diagnostic apparatus.

A pulse voltage is applied from an analog processing unit 11 to a probe 12 so that ultrasonic pulse beams are transmitted from the probe 12 toward the inside of the subject 9. The ultrasonic pulse beams transmitted to the inside of the subject 9 are reflected within the subject 9 and are returned to the probe 12. The ultrasonic pulse beams received by the probe 12 are converted into received signals and then fed to the analog processing unit 11. The analog processing unit 11 performs a so-called beamforming on the basis of the received signals. In the analog processing unit 11, the signals subjected to the beamforming process are detected and converted into digital signals. The digital signals thus converted are temporarily stored in a B-mode frame memory 14. The B-mode data stored in the B-mode frame memory 14 are read out in synchronism with data stored in a Doppler frame memory 17, a color flow frame memory 18 and the like which will be described later. The B-mode data thus read out are fed to an image display control unit 23 so as to be converted into signals for an image display. Finally, an image as illustrated in FIG. 16 is displayed on a display unit 24.

The analog processing unit 11 further transmits signals immediately after the beamforming to a Doppler processing unit 13. In the Doppler processing unit 13, the signals thus received are subjected to a quadrature detection and then converted into digital signals. The digital signals are supplied to a pulse Doppler processing unit 15 and a color flow analyzer unit 16.

An operation of a track ball 19 causes a desired point P (refer to FIG. 16) of interest to be set up on a tomographic image (B-mode image) displayed on the display unit 24. The track ball 19 produces positional information as to the point P of interest. The produced positional information is fed to a control unit 20 and a maker display control unit 21.

The track ball 19 controls the analog processing unit 11 so that a large number of times of ultrasonic pulses per unit time are transmitted, on the basis of the positional information as to the point P of interest, in a direction in which the ultrasonic pulses pass through the point P of interest, and in addition controls a flow of data outputted from the Doppler processing unit 13 in such a manner that data necessary for measurement of a blood flow velocity on the point P of interest according to the pulse Doppler scheme are fed to the pulse Doppler processing unit 15 and data necessary for formation of color flow imaging are fed to the color flow analyzer 16.

The pulse Doppler processing unit 15 determines a blood flow velocity, as to a direction in which an ultrasonic pulse beam travels, on the point P of interest designated by the operation of the track ball 19. The blood flow velocity may be evaluated with great accuracy, as mentioned above, on the basis of large numbers of data. The blood flow velocity data (Doppler data) on the point P of interest, which has been determined by the pulse Doppler processing unit 15, are temporarily stored in the Doppler frame memory 17, and then fed to the image display control unit 23.

The color flow analyzer 16 determines a blood flow distribution covering a wide range of an area within a tomographic plane. The blood flow distribution data (color data), which has been determined by the color flow analyzer 16, are temporarily stored in the color flow frame memory 18, and then fed to the image display control unit 23.

Data representative of an operational state of the track ball 19 is fed, as mentioned above, to the control unit 20 and a marker display control unit 21 as well. The marker display control unit 21 serves to perform a display control of a mark "O" indicative of the point P of interest as illustrated in FIG. 16. Data as to the mark "O" indicative of the point P of interest, which has been produced by the marker display control unit 21, is fed to the image display control unit 23, so that the mark "O" is displayed at the point P of interest positionally set up through a manipulation of the track ball 19 on a display screen of the display unit 24.

The ultrasonic diagnostic apparatus 10 shown in FIG. 1 further comprises a Doppler angle display control unit 22 having a function of evaluating the Doppler angle on the basis of the color data stored in the color frame memory 18 to display a blood flow direction (a direction of arrow 4 illustrated in FIG. 16) on the display screen, and in addition a function of suitably displaying a scale 6 illustrated in FIG. 16 on the basis of the Doppler angle thus evaluated. According to the present embodiment, the function of suitably displaying the scale 6 corresponds to an example of a blood flow velocity conversion means as set forth in claims of the present application.

According to the ultrasonic diagnostic apparatus 10 shown in FIG. 1, since it is the equivalent to the prior art in functions but the function of evaluating the Doppler angle on the basis of the color data, here there will be only given an outline as mentioned above, with respect to the explanation of the ultrasonic diagnostic apparatus 10 in its entirety. There will be described in detail an arithmetic operation for evaluating the Doppler angle by the Doppler angle display control unit 22, hereinafter.

Figure 2:
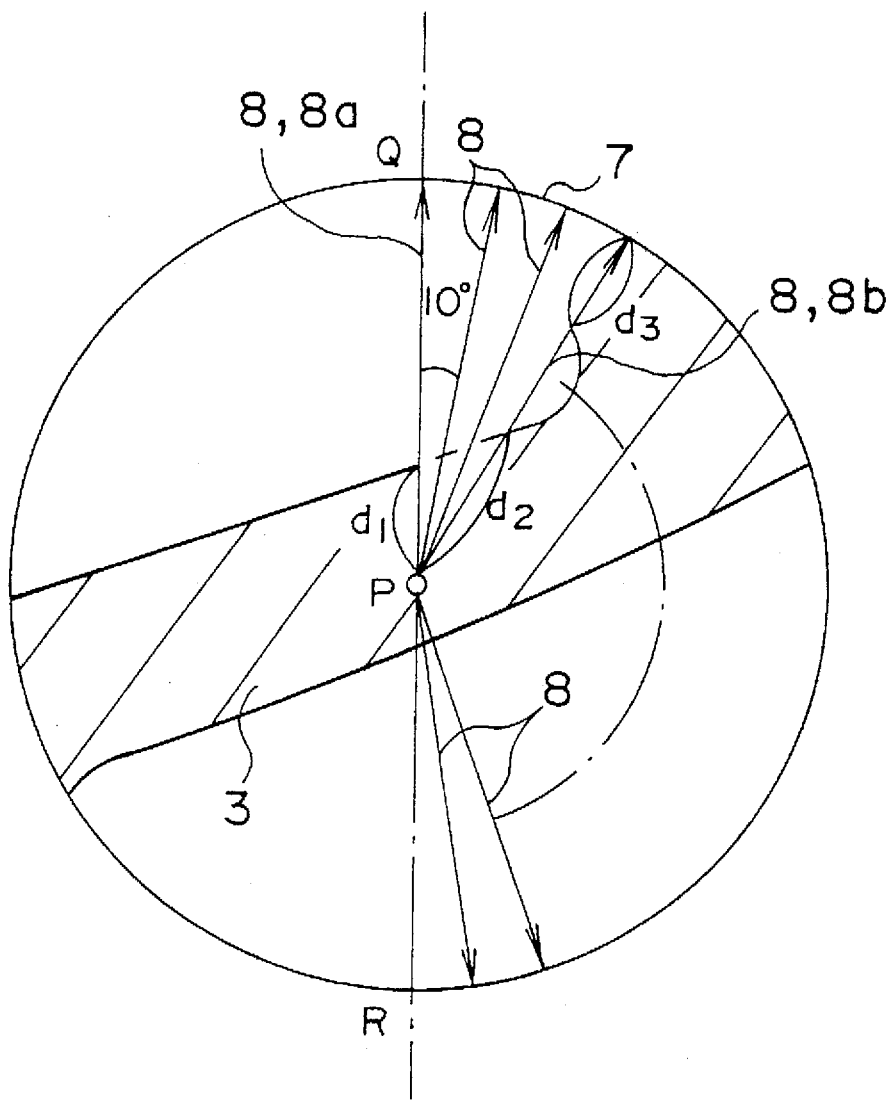
FIG. 2 is a typical illustration of the periphery of a point P of interest to be observed in a B-mode image shown in FIG. 16.

FIG. 2 is a typical illustration of the periphery of a point P of interest to be observed in a B-mode image 2 shown in FIG. 16.

Here, in the inner area of a circle 7 with the point P of interest illustrated with the mark "O" in FIG. 2 in the center, there are considered a plurality of segments 8 radially extending to 18 directions starting from a direction (referred to as a PQ direction) directed from the point P of interest to the probe 2 (see FIG. 1) up to a direction inclined by 10° with respect to a direction (a PR direction) in which the ultrasonic pulse beam travels, which directions are sequentially shifted 10° by 10°. The evaluation value representative of a probability of a blood flow direction is determined for each segment on the basis of the color data on pixels arranged along each of the segments 8. The direction corresponding to the maximum evaluation value from among the evaluation values of the respective segments is determined as the blood flow direction. The pulse Doppler processing unit 15 determines whether the component of the blood flow, which is involved in the direction by the ultrasonic pulse beam, is of plus or minus. Therefore, to determine the Doppler angle, it is sufficient to perform an arithmetic operation to determine the evaluation values on a plurality of segments radially extending within the limits of 180° as illustrated in FIG. 2.

Figure 3:
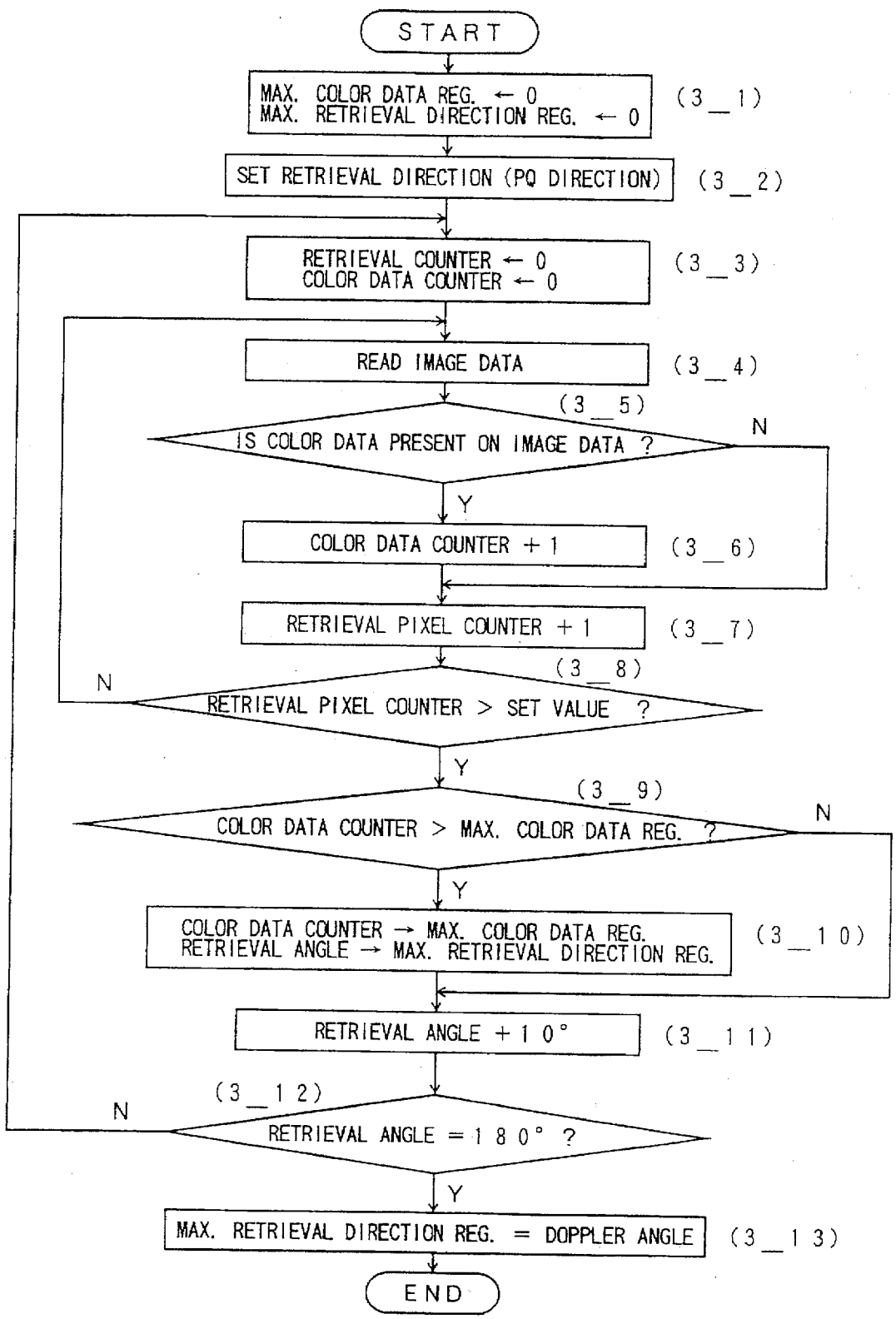
FIG. 3 is a flowchart showing a first example as to a processing procedure to evaluate a Doppler angle.

FIG. 3 is a flowchart showing a first example as to a processing procedure to evaluate a Doppler angle in accordance with the Doppler angle display control unit 22 shown in FIG. 1. FIG. 4 is an illustration showing a list for registers and the like appearing in the flowchart of FIG. 3. Here, there is adopted as the evaluation value the number of pixels to which color data are appended, of all the pixels arranged on each of segments 8 illustrated in FIG. 2.

The color data is data indicating that the blood flow exists in the associated pixel. The pixel to which no color data is appended means a pixel in which no blood flow exists, or a pixel which is associated with one wherein even if the blood flow exists therein, the blood flow velocity is less than a predetermined blood flow velocity and it may be considered that no blood flow exists in analysis of the color flow analyzer unit 16 (cf. FIG. 1). The pixel to which color data is appended means a pixel in which a blood flow having a predetermined blood flow velocity or more exists. The value of the color data corresponds to the blood flow velocity of the associated pixel. It should be noticed, however, that as mentioned above, the color data involves a remarkably large error and thus the blood flow velocity represented by the color data is an approximation.

In step $3_13 1$ of FIG. 3, for initializing, zeros are stored in a maximum color data register and a maximum retrieval direction register. The maximum color data register is a register for storing, when the number of pixels involving color data, of all the pixels arranged on the segments 8 (cf. FIG. 2), is added up for each segment, the maximum number of pixels. The maximum retrieval direction register stores a direction (a retrieval angle) in which a segment, which is involved in the largest number of pixels involving color data, of all the segments 8, extends.

Next, in step $3\_2$, a retrieval direction is initialized with a PQ direction. The process goes to step $3\_3$ in which for initializing, zeros are stored in a retrieval pixel counter and a color data counter. The retrieval pixel counter and the color data counter serve as working areas in retrieval along each of the respective segments 8.

In step $3\_4$, a pixel of image data is read along the the segment 8 on which a retrieval is now intended to be carried out, sequentially starting from the nearer one to the point P of interest. In step $3\_5$, it is determined as to whether the color data exists in the image data thus read. When the color data exists in the image data, the process goes to step $3\_6$ in which the content of the color data counter is incremented by one, and further goes to step $3\_7$ in which the content of the retrieval pixel counter is incremented by one. In step $3\_5$, when no color data exists in the image data, the process skips step $3\_6$ and goes to step $3\_7$ in which the content of the retrieval pixel counter is incremented by one.

In step $3\_8$, it is determined as to whether the value of the retrieval pixel counter exceeds a set value. The set value corresponds to a radius (a distance between the point P of interest and the circle 7; a length of the respective segment 8) of the circle 7 illustrated in FIG. 2 taking one pixel as a unit. What is meant by the fact that the value of the retrieval pixel counter exceeds a set value is the termination of a retrieval up to the position of the circle 7 along the segment 8. Thus, the process goes to step $3\_9$. When the value of the retrieval pixel counter is below a set value, the process returns to step $3\_4$ in which read is image data of the pixel adjacent to the end being apart from the point P of interest along the segment with respect to the pixel associated with the image data previously read. The above-mentioned processes are repeatedly performed, hereinafter.

In step $3\_8$, when the termination of a retrieval as to the segment is detected, the process goes to step $3\_9$. At that time, the content of the color data counter indicates the number of pixels involving color data of all the pixels existing on the segment 8. In other words, with a length expressed by providing width of a pixel as a unit, for example, in case of the segments $8a$ and $8b$ shown in FIG. 2, the values of the color data counter are $d_1$ and $d_2+d_3$, respectively.

In step $3\_9$, the value of the color data counter, namely, the number of pixels to which color data arranged on the segment now retrieved is appended, is compared with the value of the maximum color data register, namely, the maximum value of all the number of pixels to which color data is appended on the segments previously retrieved. When the number of pixels presently determined is larger than the previous maximum value, the process goes to step $3\_10$ in which the value of the color data counter is stored in the maximum color data register, and in addition the direction (retrieval angle) of the segment presently determined is stored in the maximum retrieval direction register. In step $3\_9$, when the previous maximum value is larger than the number of pixels presently determined, the process skips step $3\_10$.

In step $3\_11$, the retrieval angle is altered by 10°. In step $3\_12$, it is determined as to whether alteration of the retrieval angle by 10° causes the retrieval angle to reach 180°, in other words, as to whether the direction to be retrieved next is a PR direction shown in FIG. 2. As a result, if it is less than 180°, the process returns to step $3\_3$. Thereafter, the retrieval is carried out as to a direction which is different from the previous retrieval direction by 10°.

In step $3\_12$, when it is determined that the retrieval angle reaches 180°, the process goes to step $3\_13$ in which the Doppler angle is detected on the basis of the retrieval angle stored in the maximum retrieval direction register.

The Doppler angle display control unit 22 varies display information of the scale 6 shown in FIG. 16 on the basis of the Doppler angle thus determined, and transmits information as to the Doppler angle and display information of the scale 6 to the image display control unit 23. The image display control unit 23 causes arrow 4 directed to the blood flow direction illustrated in FIG. 16 and the suitable scale 6 to be displayed on the display screen of the display unit 24 on the basis of those information messages.

In this manner, according to the present embodiment, the evaluation value is determined through counting the number of pixels involving color data of all the pixels arranged on each of the segments 8 shown in FIG. 2, and the direction corresponding to the maximum evaluation value is automatically detected in the form of the blood flow direction, thereby performing the conversion of the display and the blood flow velocity. This feature makes it possible for an operator or observer to omit the input operation for the Doppler angle, and thus to provide an apparatus which is excellent in operability.

Figure 5:
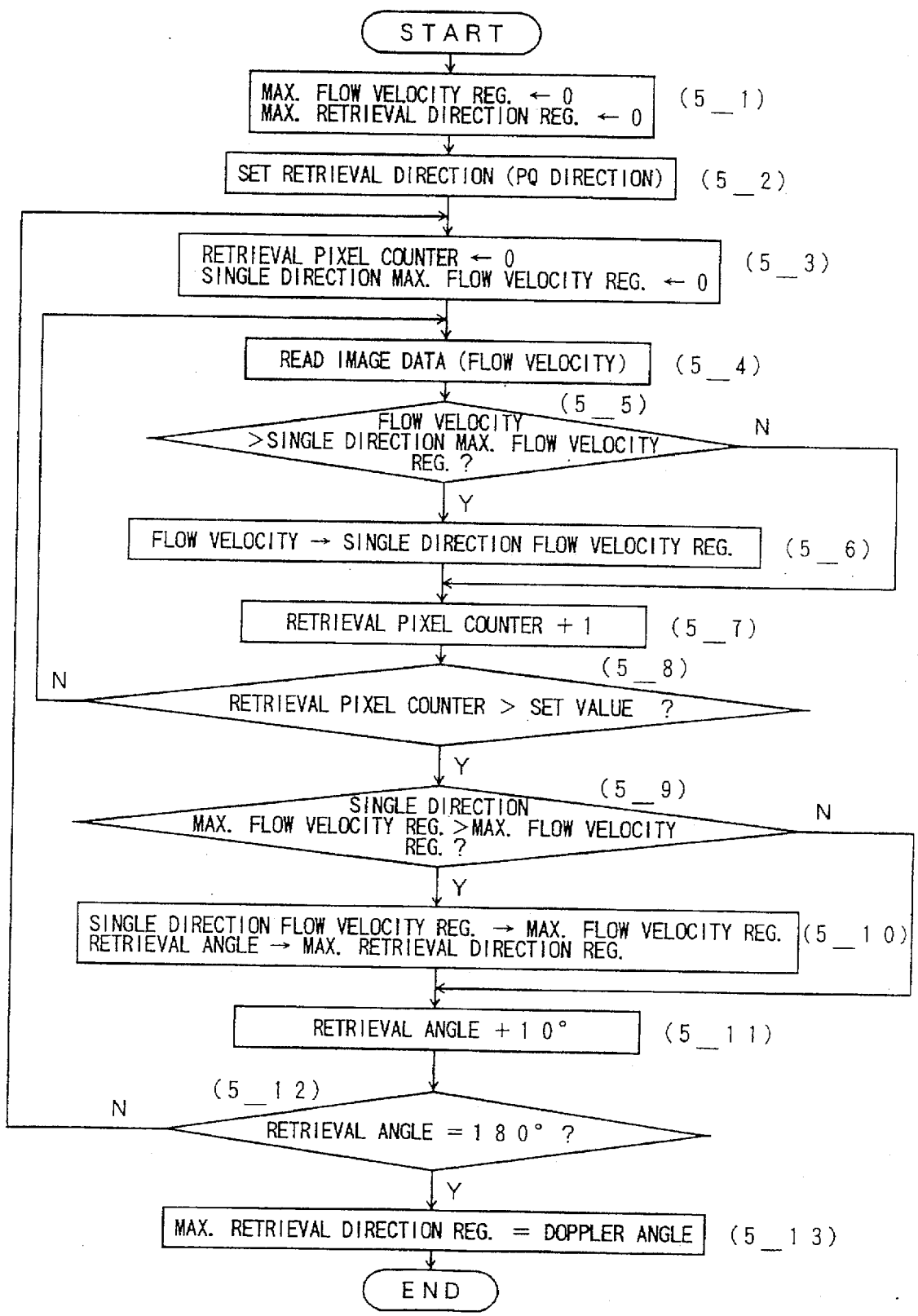
FIG. 5 is a flowchart showing a second example as to a processing procedure to evaluate a Doppler angle.

FIG. 5 is a flowchart showing a second example as to a processing procedure to evaluate a Doppler angle in accordance with the Doppler angle display control unit 22 shown in FIG. 1. FIG. 6 is an illustration showing a list for registers and the like appearing in the flowchart of FIG. 5. Here, there is adopted as the evaluation value the value of color data corresponding to the maximum flow velocity on each segment, of all the color data which are appended to the pixels arranged on each of segments 8 illustrated in FIG. 2.

In step 5_1 of FIG. 5, for initializing, zeros are stored in a maximum flow velocity register and a maximum retrieval direction register. The maximum flow velocity register is a register for storing color data indicative of the maximum flow velocity, of the pixels arranged on the segments 8 (cf. FIG. 2). The maximum retrieval direction register stores a direction (a retrieval angle) in which a segment, which is involved in color data indicative of the maximum flow velocity, of all the segments 8, extends.

Next, in step 5_2, a retrieval direction is initialized with a PQ direction. The process goes to step 5_3 in which for initializing, zeros are stored in a retrieval pixel counter and a single direction maximum flow velocity register. The retrieval pixel counter and the single direction maximum flow velocity register serve as working areas in retrieval along each of the respective segments 8.

In step 5_4, a pixel of image data is read along the the segment 8 on which a retrieval is now intended to be carried out, sequentially starting from the nearer one to the point P of interest. In step 5_5, the flow velocity represented by the color data appended to the image data is compared with the content of the single direction maximum flow velocity register. When the flow velocity now read is larger than the flow velocity value stored in the single direction maximum flow velocity register, the process goes to step 5_6 in which the flow velocity now read is stored in the single direction maximum flow velocity register, and further goes to step 5_7 in which the content of the retrieval pixel counter is incremented by one. In step 5_5, when the flow velocity value stored in the single direction maximum flow velocity register is larger than the flow velocity now read, the process skips step 5_6 and goes to step 5_7 in which the content of the retrieval pixel counter is incremented by one.

In step 5_8, it is determined as to whether the value of the retrieval pixel counter exceeds a set value. The set value corresponds to a radius of the circle 7 illustrated in FIG. 2. When the value of the retrieval pixel counter exceeds a set value, the process returns to step 5_4 in which read is image data (flow velocity) of the pixel adjacent to the end being apart from the point P of interest along the segment with respect to the pixel associated with the image data (flow velocity) previously read. The above-mentioned processes are repeatedly performed, hereinafter. In step 5_8, when the termination of a retrieval as to the segment is detected, the process goes to step 5_9. In step 5_9, the value of the single direction maximum flow velocity register, namely, the maximum value of color data of all the color data on pixels arranged on the segment now retrieved, is compared with the value of the maximum flow velocity register, namely, the maximum value of color data on the segments previously retrieved. When the maximum value of color data now determined is larger than the previous maximum value, the process goes to step 5_10 in which the value of the single direction maximum flow velocity register is stored in the maximum flow velocity register, and in addition the direction (retrieval angle) of the segment presently determined is stored in the maximum retrieval direction register. In step 5_9, when the previous maximum value is larger than the maximum value presently determined, the process skips step 5_13 10.

In step 5_11, the retrieval angle is altered by 10°. In step 5_12, it is determined as to whether alteration of the retrieval angle by 10° causes the retrieval angle to reach 180°, in other words, as to whether the direction to be retrieved next is a PR direction shown in FIG. 2. As a result, if it is less than 180°, the process returns to step 5_3. Thereafter, the retrieval is carried out as to a direction which is different from the previous retrieval direction by 10°.

In step 5_12, when it is determined that the retrieval angle reaches 180°, the process goes to step 5_13 in which the Doppler angle is detected on the basis of the retrieval angle stored in the maximum retrieval direction register.

With respect to an operation of the Doppler angle display control unit 22 hereinafter, it is the similar to the matter of the first example explained referring to FIG. 3.

In this manner, according to the present embodiment, color data having the maximum value of all the color data associated with pixels arranged on each of the segments 8 shown in FIG. 2 is adopted as the evaluation value, and the direction corresponding to the maximum evaluation value is automatically detected in the form of the blood flow direction, thereby performing the conversion of the display and the blood flow velocity. Thus, in a similar fashion to that of the first example explained referring to FIG. 3, it is possible to determine the proper blood flow velocity on the point P of interest without the input operation for the Doppler angle, and thus to provide an apparatus which is excellent in operability.

Figure 7:
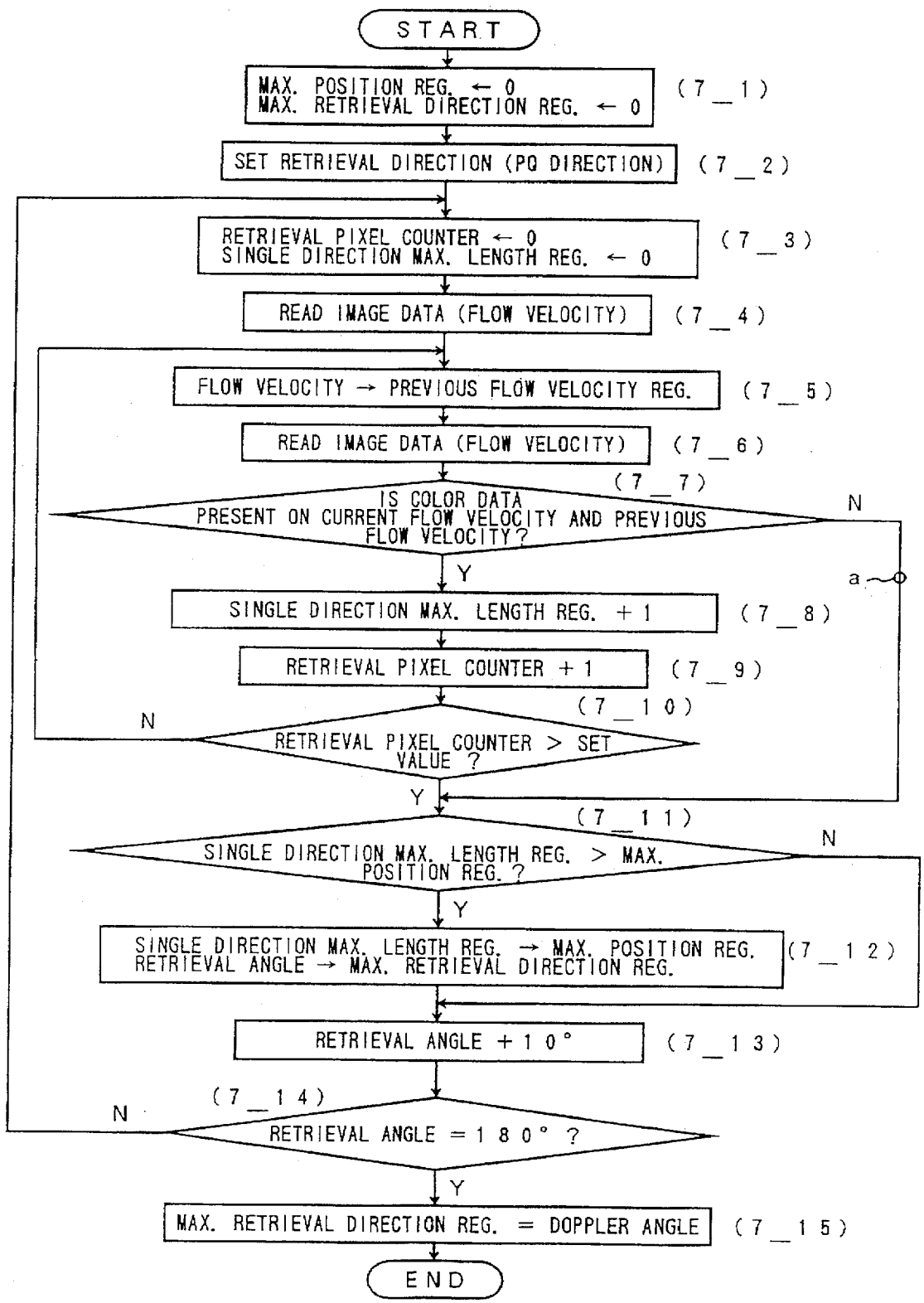
FIG. 7 is a flowchart showing a third example as to a processing procedure to evaluate a Doppler angle.
Figures 8, 9:
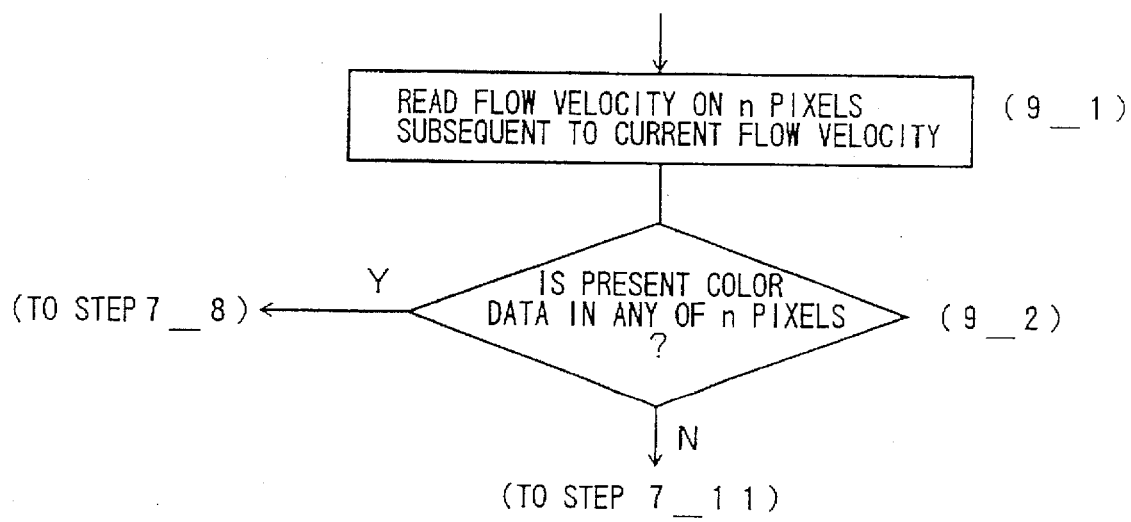
FIG. 8 is an illustration showing a list for registers and the like appearing in the flowchart of FIG. 7.
FIG. 9 is a flowchart useful for understanding a modification of the third example shown in FIG. 7 by way of example.

FIG. 7 is a flowchart showing a second example as to a processing procedure to evaluate a Doppler angle in accordance with the Doppler angle display control unit 22 shown in FIG. 1. FIG. 8 is an illustration showing a list for registers and the like appearing in the flowchart of FIG. 7. Here, there is adopted as the evaluation value the number of pixels to which color data are continuously appended, of all the pixels arranged on each of segments 8 illustrated in FIG. 2. Specifically, in case of the segments 8a and 8b illustrated in FIG. 2, length $d_1$ and length $d_2$ become the evaluation values as to the segments 8a and 8b, respectively.

In step 7_1 of FIG. 7, for initializing, zeros are stored in a maximum position register and a maximum retrieval direction register. The maximum position register is a register for storing the maximum number on the segments 8 of all the number of color data indicative of the number of pixels involving the color data counting the point P of interest as the starting point, of all the pixels arranged on the segments 8 (cf. FIG. 2). The maximum retrieval direction register stores a direction (a retrieval angle) in which a segment, which is associated with the maximum number, of all the segments 8, extends.

Next, in step 7_2, a retrieval direction is initialized with a PQ direction. The process goes to step 7_3 in which for initializing, zeros are stored in a retrieval pixel counter and a single direction maximum length register. The retrieval pixel counter and the single direction maximum length register serve as working areas in retrieval along each of the respective segments 8.

In step 7_5, a pixel of image data on the point A of interest is read and stored in a previous flow velocity register. The previous flow velocity register also serves as working areas in retrieval along each of the respective segments 8.

In step 7_6, a pixel of image data is read along the the segment 8 on which a retrieval is now intended to be carried out, sequentially starting from the nearer one to the point P of interest. Here, the image data (flow velocity) read in step 7_6 is referred to as "current flow velocity".

In step 7_7, it is determined as to whether color data exist on both the current flow velocity and the flow velocity (that is, the flow velocity stored in the previous register) on the pixel at the end of the point P of interest, which is adjacent to the pixel associated with the current flow velocity. The existence of the color data on both kinds of flow velocity means that the color data continues. Thus, the process goes to step 7_8 in which the value of the single direction maximum length register is incremented by one, and further goes to step 7_9 in which the value of the retrieval pixel counter is incremented by one. Further, the process goes to step 7_10. In step 7_10, it is determined as to whether the value of the retrieval pixel counter exceeds a set value. The set value corresponds to a radius of the circle 7 illustrated in FIG. 2. When the value of the retrieval pixel counter exceeds the set value, the process goes to step 7_11. On the other hand, when the value of the retrieval pixel counter is less than the set value, the process returns to step 7_5 in which the current flow velocity previously read in step 7_6 is stored in the previous flow velocity register, and goes to step 7_6 in which read is image data (flow velocity) of the pixel at the end being apart from the point P of interest along the segment now on retrieval, which is adjacent to the pixel associated with the current flow velocity previously read in step 7_6. The above-mentioned processes are repeatedly performed, hereinafter.

On the other hand, in step 7_7, when it is determined that the color data does not continue, the process jumps to step 7_11, since there is no need to proceed with the retrieval on the segment. In step 7_11, the value of the single direction maximum length position register is compared with the value of the maximum length register. In other words, the number of pixels to which color data are continuously appended starting from the point A of interest on the segment 8 now retrieved is the maximum value of all the number of pixels to which color data are continuously appended starting from the point A of interest on each of the segments 8 previously retrieved.

In step 7_11, when the value of single direction maximum length register is larger than the value of the maximum length position register, in other words, when the number of pixels now determined is larger than the previous maximum value, the process goes to step 7_12 in which the value of the single direction maximum flow velocity register is stored in the maximum length position register, and in addition the direction (retrieval angle) of the segment presently determined is stored in the maximum retrieval direction register. In step 7_11, when the previous maximum value is larger than the maximum value presently determined, or when they are equal to each other, the process skips step 7_12. In step 7_13, the retrieval angle is altered by 10°.

In step 7_14, it is determined as to whether alteration of the retrieval angle by 10° causes the retrieval angle to reach 180°, in other words, as to whether the direction to be retrieved next is a PR direction shown in FIG. 2. As a result, if it is less than 180°, the process returns to step 7_3. Thereafter, the retrieval is carried out as to a direction which is different from the previous retrieval direction by 10°.

In step 7_14, when it is determined that the retrieval angle reaches 180°, the process goes to step 7_15 in which the Doppler angle is detected on the basis of the retrieval angle stored in the maximum retrieval direction register.

With respect to an operation of the Doppler angle display control unit 22 hereinafter, it is the similar to the matter of the first example explained referring to FIG. 3.

In this manner, according to the present embodiment, the number of pixels involving color data which are continuously arranged starting from the point A of interest on each of the segments 8 shown in FIG. 2 is adopted as the evaluation value, and the direction corresponding to the maximum evaluation value is automatically detected in the form of the blood flow direction, thereby performing the display of the arrow 4 shown in FIG. 16, and the conversion of the scale 6 and display. Thus, in a similar fashion to that of the first and second examples explained referring to FIGS. 3 and 5, it is possible to determine the proper blood flow velocity on the point P of interest without manually setting the Doppler angle, and thus to provide an apparatus which is excellent in operability.

FIG. 9 is a flowchart useful for understanding a modification of the third example shown in FIG. 7 by way of example. Here only portions to be added to the flowchart of FIG. 7 are shown.

The partial flowchart shown in FIG. 9 is added to the portion a shown in FIG. 7.

In step 7_7 shown in FIG. 7, in a case where there exists no color data on either of the current flow velocity and the previous flow velocity stored in the previous flow velocity register, the process goes to step 9_1 in which read is the flow velocity of a predetermined number of n pieces of pixels, which sequentially continue, subsequent to the pixels associated with the current flow velocity, and then goes to step 9_2 in which it is determined as to whether color data exists on any of those n pixels.

In a case where color data exists on any of n pixels, in other words, in a case where the pixels on which no color data exists are less than n pixels, it is regarded as the matter that color data continue even on those pixels, and thus the process goes to step 7_8. When no color data exists on any of n pixels, it is determined that the continuity of the color data has terminated, and then the process goes to step 7_11.

As mentioned above, the color data includes a remarkably large errors. Therefore, it happens that even in an area in which the blood flow exists indeed, there exist a lot of pixels on which no color data exists. In such a case, according to the modification as shown in FIG. 9 by way of example, even if there exists no color data during a short continuous pixels period such as the order of n pixels or less, when the color data exist again thereafter, it is considered that the color data exists even in a section in which no color data exists indeed. This feature makes it possible to detect the Doppler angle almost independently of noises.

Figure 10:
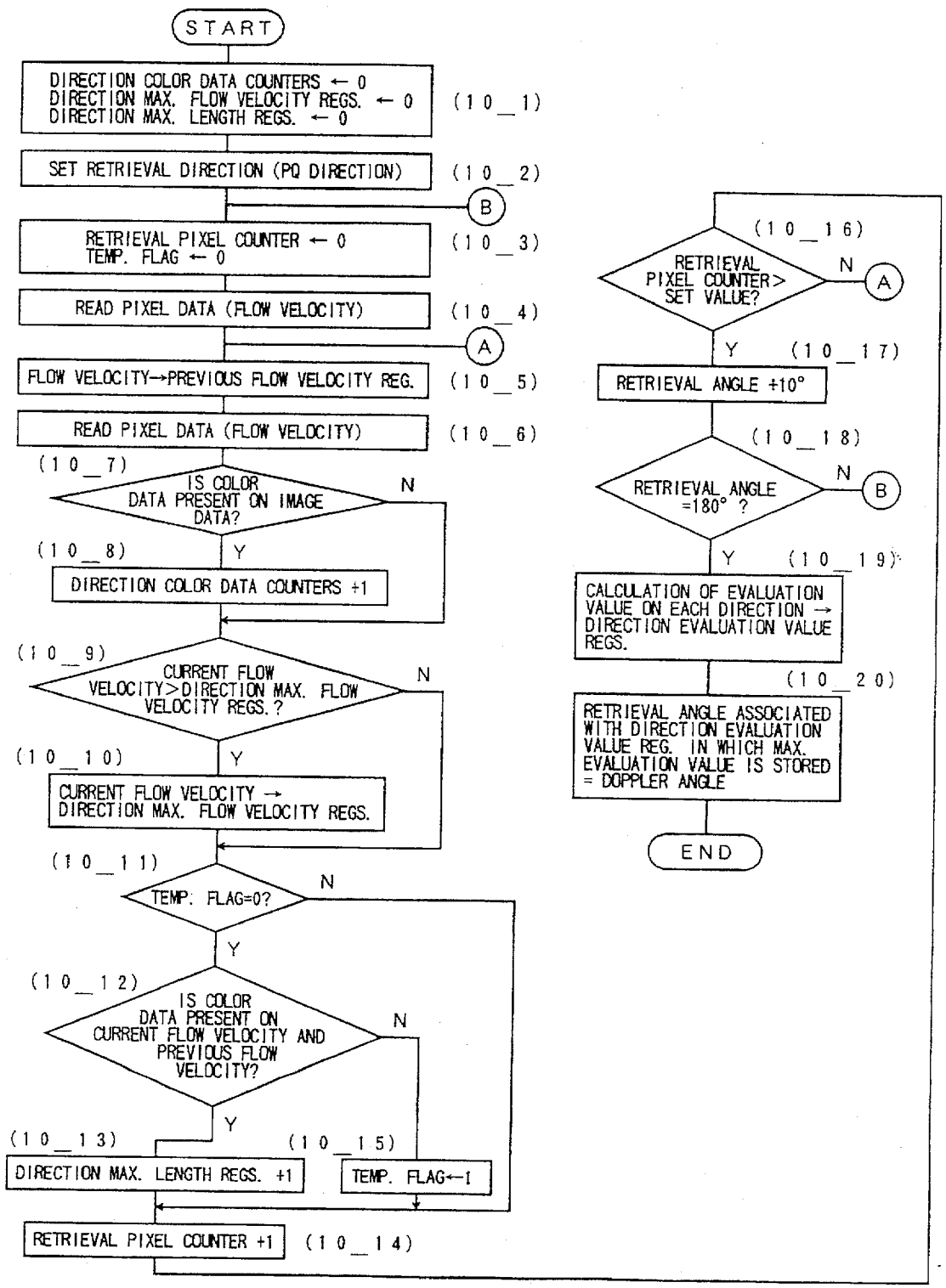
FIG. 10 is a flowchart showing a fourth example as to a processing procedure to evaluate a Doppler angle.

FIG. 10 is a flowchart showing a fourth example as to a processing procedure to evaluate a Doppler angle in accordance with the Doppler angle display control unit 22 shown in FIG. 1. FIG. 11 is an illustration showing a list for registers and the like appearing in the flowchart of FIG. 10. Here, there are adopted as the evaluation values syntheses of the respective evaluation values shown in FIGS. 3, 5 and 7.

Here, as shown in FIG. 11, there are provided for each segment 8 shown in FIG. 2 the associated direction color data counter, the associated direction maximum flow velocity register, the associated direction maximum length register and the associated direction evaluation value register.

In step 10_1 of FIG. 10, for initializing, zeros are stored in the direction color data counters, the direction maximum flow velocity registers and the direction maximum length registers. The direction color data counter is a register for storing the number of pixels involving color data, of all the pixels arranged on each of the segments 8 (cf. FIG. 2). The direction maximum flow velocity register stores color data indicative of the maximum flow velocity on each direction, of all the pixels arranged on each of the segments 8. The direction maximum length register serves to store the number of pixels, which continuously involve color data starting from the point A of interest, of all the pixels arranged on each of the segments 8.

Next, in step 10_2, a retrieval direction is initialized with a PQ direction. The process goes to step 10_3 in which for initializing, zero is stored in a retrieval pixel counter and zero is set to a temporary flag. The retrieval pixel counter and the temporary flag serve as working areas in retrieval along each of the segments 8.

In step 10_4, a pixel of image data (flow velocity) on the point A of interest is read, and in step 10_5 the flow velocity thus read is stored in a previous flow velocity register. The previous flow velocity register also serves as working areas in retrieval along each of the segments 8. In step 10_6, a pixel of image data is read along the the segment 8 on which a retrieval is now intended to be carried out, sequentially starting from the nearer one to the point P of interest. Here, the image data (flow velocity) read in step 10_6 is referred to as "current flow velocity".

In step 10_7, it is determined as to whether color data (flow velocity) exists on the image data. When the color data exists on the image data, the process goes to step 10_8 in which incremented by one is the value of the direction color data counter associated with the direction (segment) now on retrieval, of all the direction color data counters shown in FIG. 11. In step 10_7, when no color data exists on the image data, the process skips step 10_8.

In step 10_9, the current flow velocity is compared with the value of the direction maximum flow velocity register associated with the direction (segment) now on retrieval, of all the direction maximum flow velocity registers shown in FIG. 11. When the current flow velocity is larger than the value of the direction maximum flow velocity register associated with the direction now on retrieval, the process goes to step 10_10 in which the current flow velocity is stored in the direction maximum flow velocity register associated with the direction now on retrieval, and goes to step 10_11. In step 10_9, on the other hand, when the current flow velocity is less than the value of the direction maximum flow velocity register associated with the direction now on retrieval, or they are equal to each other, the process skips step 10_10 and goes to step 10_11.

In step 10_11, it is determined as to whether the temporary flag is zero. When the temporary flag is given by "1", the process goes to step 10_14. On the other hand, when the temporary flag is given by zero, the process goes to step 10_12 in which it is determined as to whether the color data exist on both the current flow velocity and the previous flow velocity (the flow velocity on the pixel at the end of the point P of interest, which is adjacent to the pixel associated with the current flow velocity, that is, the value of the previous register). The existence of the color data on both kinds of flow velocity means that the color data continues from the point P of interest. Thus, the process goes to step 10_13 in which the value of the direction maximum length register associated with the current retrieval direction, of all the direction maximum length registers is incremented by one, and further goes to step 10_14.

On the other hand, in step 10_12, when it is determined that the color data does not continue, the process jumps to step 10_15, since there is no need to perform the processing in the steps 10_12 and 10_13 on the segment hereafter, in which step "1" is stored in the temporary flag to inhibit the processing in the steps 10_12 and 10_13 on the segment, and goes to step 10_14.

In step 10_14, it is determined as to whether the value of the retrieval pixel counter exceeds a set value. The set value corresponds to a radius of the circle 7 illustrated in FIG. 2. When the value of the retrieval pixel counter exceeds the set value (this means the termination of the retrieval on the associated direction), the process goes to step 10_17. On the other hand, when the value of the retrieval pixel counter is less than the set value, the process returns to step 10_5 in which the current flow velocity previously read in step 10_6 is stored in the previous flow velocity register, and goes to step 10_6 in which read is image data (flow velocity) of the pixel at the end being apart from the point P of interest along the segment now on retrieval, which is adjacent to the pixel associated with the current flow velocity previously read in step 10_6. The above-mentioned processes are repeatedly performed, hereinafter.

On the other hand, in step 10_16, when it is determined that the retrieval on the segment is terminated, the process goes to step 10_17 in which the retrieval angle is altered by 10°. In 10_18, it is determined as to whether alteration of the retrieval angle by 10° causes the retrieval angle to reach 180°, in other words, as to whether the direction to be retrieved next is a PR direction shown in FIG. 2. As a result, if it is less than 180°, the process returns to step 10_3. Thereafter, the retrieval is carried out as to a direction which is different from the previous retrieval direction by 10°.

In step 10_18, when it is determined that the retrieval angle reaches 180°, the process goes to step 10_19 in which the calculation of the evaluation values on the respective directions is performed. Here, the evaluation value on each of the directions is determined through the weighted addition for each direction of the value of the associated direction color data counter, the value of the associated direction maximum flow velocity register and the associated direction maximum length register. The evaluation value on each of the directions thus determined is stored in the associated direction evaluation value register.

In this manner, when the evaluation value on each direction is determined and stored in the associated direction evaluation value register, the process goes to step 10_20 in which the direction evaluation value register, which stores the maximum evaluation value of all the evaluation values stored in the direction evaluation value registers, is searched so that a Doppler angle is detected on the basis of the retrieval angle associated with the direction evaluation value register in which the maximum evaluation value is stored.

With respect to an operation of the Doppler angle display control unit 22 (cf. FIG. 1) hereinafter, it is the similar to the matter of the above-mentioned respective examples. According to the example explained referring to FIG. 10, the evaluation values are determined on the basis of a plurality of kinds of index. Thus, it is possible to determine the Doppler angle with greater accuracy, thereby evaluating the blood flow velocity with greater accuracy.

Incidentally, while there exists the exemplary modification for the example shown in FIG. 10 in a similar fashion to the matter of the exemplary modification shown in FIG. 9 for the example shown in FIG. 7, it is simply involved in such a matter that the partial flowchart, which is similar to that shown in FIG. 9, is added to the flowchart shown in FIG. 10. Accordingly, the illustration and the explanation for the exemplary modification for the example shown in FIG. 10, which is similar to that of FIG. 9, will be omitted.

FIG. 12 is a block diagram of an ultrasonic diagnostic apparatus according to an another illustrative embodiment of the present invention. In FIG. 12, the same parts are denoted by the same reference numbers as those of FIG. 1. Only different points therebetween will be described.

An ultrasonic diagnostic apparatus 10' shown in FIG. 12 comprises, instead of the Doppler angle display control unit 22 in the ultrasonic diagnostic apparatus 10 shown in FIG. 1, a Doppler angle display control unit 22' to which output data of the image display control unit 23 is fed.

The output data of the image display control unit 23, which is fed to the Doppler angle display control unit 22', is originally color data which is evaluated by the color flow analyzer unit 16 and is stored in color flow frame memory 18. Such color data is converted, by the image display control unit 23, into a so-called raster scan data suitable for the display.

Figure 13:
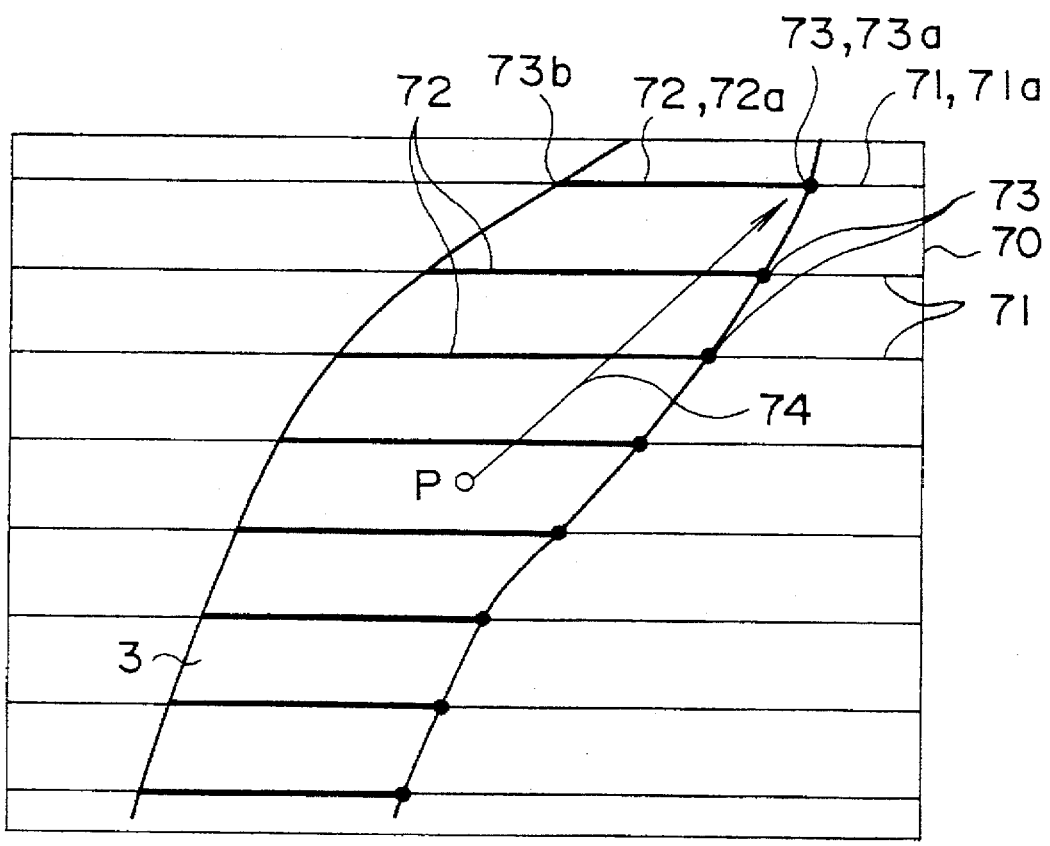
FIG. 13 is a typical illustration of the periphery of a point P of interest to be observed in a B-mode image shown in FIG. 16.

FIG. 13 is a typical illustration of the periphery of a point P of interest to be observed in a B-mode image shown in FIG. 16.

Here, there are determined: segment areas 72 on each of which color data exists along the associated one of a plurality of segments 71 extending in the lateral direction mutually in parallel within a rectangular area 70, shown in FIG. 13; one of the end points 73 of each of the segment areas 72; a distance between the point P of interest and each of the end points 73; and the direction, as the blood flow direction, directed from the point P of interest toward the end point 73 located at the farthest position from the point P of interest, of all the end points 73.

According to the example shown in FIG. 13, the end point 73a on the segment area 72a involving the continuous color data is located at the farthest position from the point P of interest. Thus, the direction of arrow 74 directed from the point P of interest toward the end point 73a is determined as the blood flow direction. In this case, while it happens that the blood flow direction is determined with some error, such an error is within a permissible range in the practical use. Further, according to this arithmetic scheme, different from the schemes according to the examples as mentioned above in which the retrieval is carried out along the segments extending radially from the point P of interest, it is simply to perform the retrieval in a horizontal direction along the flow of the raster data. Thus, it is possible to perform the high speed arithmetic operation.

Figure 14:
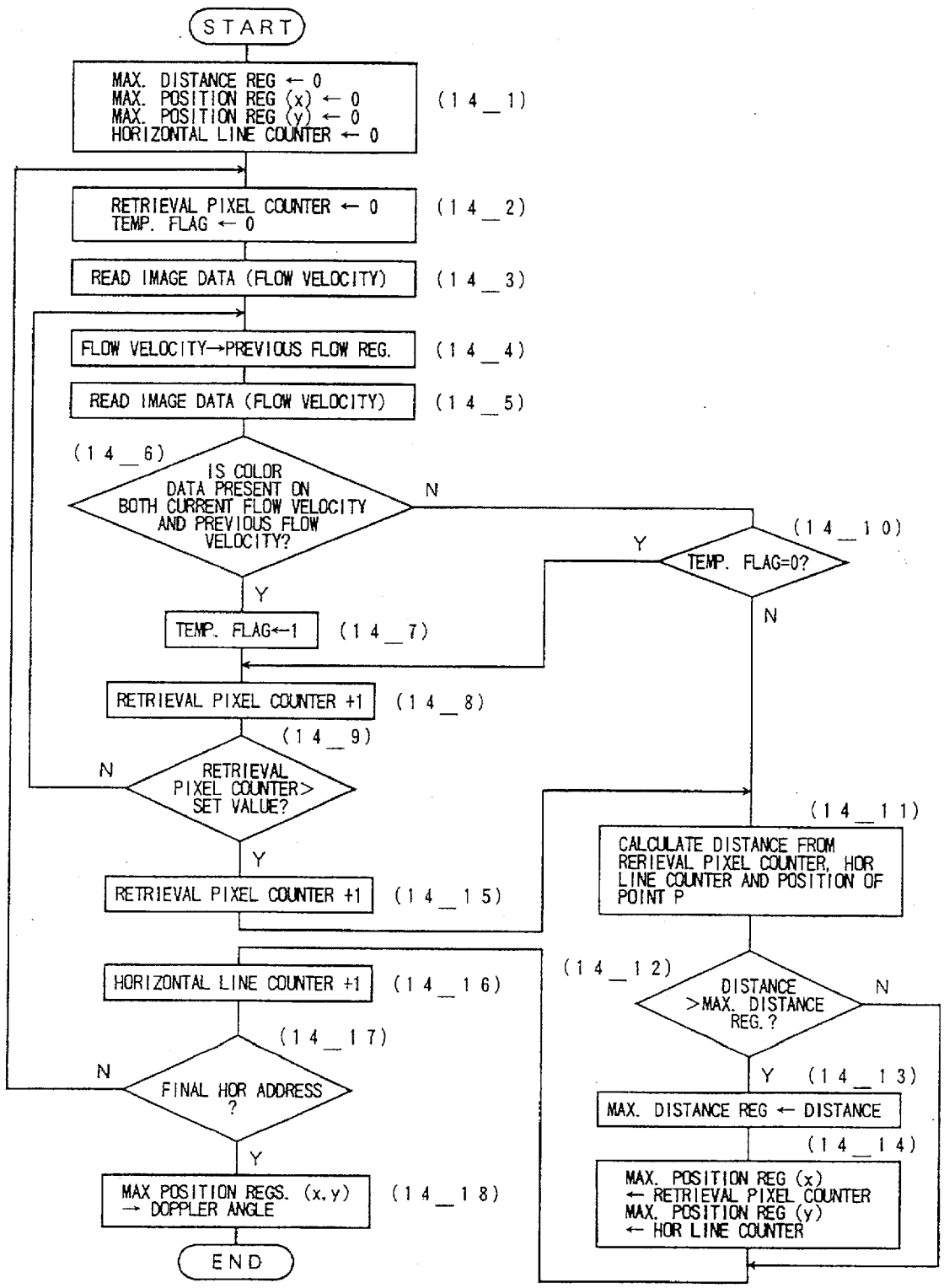
FIG. 14 is a flowchart showing a processing procedure to evaluate a Doppler angle.

FIG. 14 is a flowchart showing a processing procedure to evaluate a Doppler angle using the Doppler angle display control unit 22' shown in FIG. 12, explained referring to FIG. 13. FIG. 15 is an illustration showing a list for registers and the like appearing in the flowchart of FIG. 14.

First, in step 14_1, for initializing, zeros are stored in the maximum distance register, the maximum position register (x), the maximum position register (y) and the horizontal line counter. The maximum distance register is a register for storing the maximum distance of all the distances between the point P of interest and the respective end points 73 of the segment areas 72 on the segments (lines) on which the retrieval have been terminated, of all the segments (lines) 71 shown in FIG. 13. The horizontal line counter is a register for the numbers of the segments (lines) 71 which are now subjected to the retrieval, of all the segments (lines) 71 shown in FIG. 13. The maximum position register (x) and the maximum position register (y) store coordinates of the end point 73 of the segment area 72 on the segment (line) 71 associated with the maximum distance stored in the maximum distance register.

Next, in step 14_2, zeros are stored in a retrieval pixel counter and a temporary flag. The retrieval pixel counter, the temporary flag and the previous flow velocity register (which will be described later) serve as working areas for the retrieval for each segment (line) 71. It is assumed that the retrieval for each segment (line) 71 is performed for each pixel sequentially from the left end of the rectangular area 70 shown in FIG. 13 toward the right end thereof.

In step 14_3, read is image data (flow velocity) of a pixel located at the left end of the rectangular area 70 on the segment (line) 71 which are now intended to be retrieved, and in step 14_4 the flow velocity thus read is stored in a previous flow velocity register. In step 14_5, image data (flow velocity) of a pixel adjacent to the right end of the pixel involved in the previous flow velocity is read. Here, the image data (flow velocity) read in step 14_5 is referred to as "current flow velocity". In step 14_6, it is determined as to whether color data (flow velocity) exists on both the current flow velocity and the previous flow velocity. When the color data exists on both, the process goes to step 14_7 in which "1" is stored in the temporary flag.

The temporary flag is a flag indicative of as to whether the retrieval process advances up to the area in which the color data exists on the associated segment (line) 71. In step 14_8, the value of the retrieval pixel counter is incremented by one. In step 14_9, the value of the retrieval pixel counter is compared with the set value indicative of the fact that the retrieval process advances to the right end of the rectangular area 70 shown in FIG. 13. When the value of the retrieval pixel counter is less than the set value, the process returns to step 14_4 in which the current flow velocity read previously in step 14_5 is stored in the previous flow velocity register, and goes to step 14_5. In step 14_5, the image data (flow velocity) of a pixel adjacent to the right end of the pixel involved in the current flow velocity, which was previously read in step 14_5, is read as the new current flow velocity. Hereinafter, the above-mentioned processing is repeatedly carried out.

In step 14_6, when it is determined that no color data exists on at least one of both the current flow velocity and the previous flow velocity, the process goes to step 14_10 in which it is determined as to whether the temporary flag is kept zero. For example, in case of the segment (line) 71a shown in FIG. 13, the temporary flag will be kept zero, when the retrieval is implemented starting from the left end of the segment 71a toward the right end sequentially, up to the left end of the segment 73b of the segment area 72a. In step 14_10, when the temporary flag is zero, the process skips step 14_7 and goes to step 14_8.

In step 14_10, when the temporary flag is set to "1", the process goes to step 14_11, since the set "1" of the temporary flag means that for example, in case of the segment 71a shown in FIG. 13, the retrieval has reached the segment area 72a, and in addition means that in step 14_6 the color data breaks off, that is, the retrieval has reached the end point 73a. In step 14_11, the distance between the positional coordinates of the end point 73 of the segment 71 now on retrieval and the positional coordinates of the point P of interest is calculated on the basis of the value of the retrieval pixel counter in the form of the current value, the value of the horizontal line counter in the form of the current value and the positional coordinates of the point P of interest.

In step 14_12, the distance evaluated in step 14_11 is compared with the value of the maximum distance register. When the value now evaluated is larger than the value of the maximum distance register, the process goes to step 14_13 in which the value now evaluated is stored in the maximum distance register, and further goes to step 14_14 in which the value of the retrieval pixel counter, or x-coordinates of the end point 73 of the segment 71 now on retrieval is stored in the maximum position register (x), whereas the value of the horizontal line counter, or y-coordinates of the end point 73 of the segment 71 now on retrieval is stored in the maximum position register (y).

In step 14_9, when it is determined that the value of the retrieval pixel counter exceeds the set value, in other words, when the retrieval reaches the left end shown in FIG. 13 while the color data does not break off, the process also goes to step 14_11 in which the distance is calculated. In this case, however, since the retrieval pixel counter has been incremented in step 14_8, the content of the retrieval pixel counter is incremented by one in step 14_15 and then the process goes to step 14_11.

After step 14_14 the the process goes to step 14_16 in which the content of the horizontal line counter is incremented by one. In step 14_17, it is determined as to whether the retrieval has been terminated up to the final horizontal address (final segment), on the basis of the content of the horizontal line counter thus incremented. When the retrieval has not yet been terminated up to the final horizontal address, the process returns to step 14_2 to start the retrieval on the next line or segment.

In step 14_17, when it is determined that the retrieval has been terminated up to the final horizontal address, the process goes to step 14_18 in which the Doppler angle is determined on the basis of the values of the maximum position register (x) and the maximum position register (y).

With respect to an operation of the Doppler angle display control unit 22' (cf. FIG. 12) after detection of the Doppler angle, it is the similar to the matter of the above-mentioned respective examples referring to the Doppler angle display control unit 22 (cf. FIG. 1). According to the example explained here, it is possible to determine the Doppler angle in shorter time, since the retrieval on the color data is carried out in the horizontal direction in which pixel data are arranged on a raster time basis.

As mentioned above, according to the ultrasonic diagnostic apparatus of the present invention, trouble for manually setting the Doppler angle is saved thereby implementing the apparatus excellent in operability.

While the present invention has been explained with reference to the particular illustrative embodiments, it is not to be limited to those embodiments. It is to be appreciated that those skilled in the art can change or modify the embodiments within the scope and spirit of the appended claims.

I claim:

1. An ultrasonic diagnostic apparatus in which ultrasonic beams are transmitted into a subject and ultrasonic waves reflected within the subject are received thereby forming received signals, and information as to the inside of the subject is displayed on the basis of the received signals, the ultrasonic diagnostic apparatus comprising:

first blood flow velocity measurement means for evaluating on the basis of the received signals a blood flow velocity distribution covering a plurality of pixels within a tomographic plane spreading on a two-dimensional basis within the subject;

observed point setting means for optionally setting a point of interest to be observed within the tomographic plane;

second blood flow velocity measurement means for evaluating on the basis of the received signals a blood flow velocity, at the point of interest set by said observed point setting means, in a direction in which ultrasonic beams passing through the point of interest are extended, said second blood flow velocity measurement means evaluating the blood flow velocity with greater accuracy than said first blood flow velocity measurement means;

blood flow direction arithmetic means for evaluating a direction of a blood flow at the point of interest within said tomographic plane on the basis of the blood flow velocity distribution evaluated by said first blood flow velocity measurement means; and blood flow velocity conversion means for converting the blood flow velocity at the point of interest evaluated by said second blood flow velocity measurement means into a blood flow velocity in the direction of the blood flow evaluated by said blood flow direction arithmetic means.

2. An apparatus according to claim 1, wherein said blood flow direction arithmetic means evaluates, on the basis of the blood flow velocity distribution evaluated by said first blood flow velocity measurement means, a plurality of evaluation values each involved in an associated one of a plurality of segments radially extending from the point of interest within the tomographic plane, representative of a probability such that the direction in which the respective segment extends is a direction of a blood flow at the point of interest, and determines, as the direction of the blood flow, a direction in which the respective segment involved in a maximum of the plurality of evaluation values of all the plurality of segments extends.

3. An apparatus according to claim 2, wherein said blood flow direction arithmetic means evaluates a number of pixels on which the blood flow exists, said pixels being located on each of the plurality of segments extending in a predetermined area including the point of interest within the tomographic plane, for each of said plurality of segments, and uses the number of pixels as the plurality of evaluation values for each of said plurality of segments.

4. An apparatus according to claim 2, wherein said blood flow direction arithmetic means evaluates a maximum flow velocity of a plurality of the blood flow velocity messages on pixels, said pixels being located on each of the plurality of segments extending in a predetermined area including the point of interest within the tomographic plane, for each of said plurality of segments, and uses the maximum flow velocity as the plurality of evaluation values for each of said plurality of segments.

5. An apparatus according to claim 2, wherein said blood flow direction arithmetic means evaluates a distance starting from the point of interest up to the farthest pixel involved in a blood flow existence continued from the point of interest, of all the pixels on which the blood flow exist in a direction along each of the plurality of segments extending in a predetermined area including the point of interest within the tomographic plane, for each of said plurality of segments, and uses the distance thus obtained as the evaluation values.

6. An apparatus according to claim 5, wherein said blood flow direction arithmetic means regards, even if the pixels involved in the absence of the blood flow in a direction along each of the segments continue below a predetermined number, these pixels continued below the predetermined number as the pixels involved in the presence of the blood flow.

7. An apparatus according to claim 2, wherein said blood flow direction arithmetic means evaluates at least two among a number of pixels on which the blood flow exists, said pixels being located on each of the plurality of segments extending in a predetermined area including the point of interest within the tomographic plane, a maximum flow velocity of all the blood flow velocity messages on said pixels, and a distance starting from the point of interest up to the farthest pixel involved in a blood flow existence continued from the point of interest, of all the pixels on which the blood flow exist in a direction along each of the plurality of segments, for each of said plurality of segments, and determines the evaluation values for each segment on the basis of said at least two pixels.

8. An apparatus according to claim 7, wherein said blood flow direction arithmetic means regards, even if the pixels involved in the absence of the blood flow in a direction along each of the segments continue below a predetermined number, these pixels continued below the predetermined number as the pixels involved in the presence of the blood flow.

9. An apparatus according to claim 2, wherein said blood flow direction arithmetic means compares the maximum evaluation value with a predetermined threshold, and as a result when the maximum evaluation value is less than the threshold, issues information indicating that conversion of the blood flow velocity by said blood flow velocity conversion means is not feasible.

10. An apparatus according to claim 2, wherein said blood flow direction arithmetic means compares the maximum evaluation value with a predetermined threshold, and as a result when the maximum evaluation value is less than the threshold, determines that a predetermined direction within said tomographic plane is a direction of the blood flow at the point of interest.

11. An apparatus according to claim 1, wherein said blood flow direction arithmetic means determines, on the basis of the blood flow velocity distribution evaluated by said first blood flow velocity measurement means, at least one end point of each of a plurality of segment areas involved in a continuity in pixels involving the existence of a blood flow, along each of a plurality of segments extending in mutually parallel directions within said tomographic plane, and determines a direction from the point of interest toward the end point in the longest distance between the point of interest and the end point, of all the end points, as a direction of the blood flow at the point of interest.

12. An apparatus according to claim 11, wherein said blood flow direction arithmetic means regards, even if the pixels involved in the absence of the blood flow in a direction along each of the segments continue below a predetermined number, these pixels continued below the predetermined number as the pixels involved in the presence of the blood flow.

* * * * *